United States Patent [19]

Takaya et al.

[11] Patent Number: 4,994,590
[45] Date of Patent: Feb. 19, 1991

[54] RUTHENIUM-PHOSHINE COMPLEX

[75] Inventors: Hidemasa Takaya, Shiga; Kazushi Mashima, Kyoto; Hidenori Kumobayashi; Noboru Sayo, both of Kanagawa, all of Japan

[73] Assignee: Takasago International Corporation, Tokyo, Japan

[21] Appl. No.: 427,209

[22] Filed: Oct. 24, 1989

[30] Foreign Application Priority Data

Oct. 24, 1988 [JP] Japan .................. 63-267946
Sep. 16, 1989 [JP] Japan .................. 1-242604

[51] Int. Cl.$^5$ .................. C07F 15/00; C07F 9/50
[52] U.S. Cl. .................. 556/21; 556/23; 556/136
[58] Field of Search .................. 556/16, 13, 19, 20, 556/21, 22, 136

[56] References Cited

U.S. PATENT DOCUMENTS

| | | | |
|---|---|---|---|
| 3,878,122 | 4/1975 | Pennella | 536/23 X |
| 4,268,454 | 5/1981 | Pez et al. | 556/23 X |
| 4,506,030 | 3/1985 | Jones | 556/23 X |
| 4,691,037 | 9/1987 | Yoshikawa et al. | 556/23 X |
| 4,739,084 | 4/1988 | Takaya et al. | 556/21 |
| 4,739,085 | 4/1988 | Takaya et al. | 556/21 |

Primary Examiner—Arthur C. Prescott
Attorney, Agent, or Firm—Sughrue, Mion, Zinn, Macpeak & Seas

[57] ABSTRACT

A ruthenium-phosphine complex represented by formula (I)

$$[RuX_l(L)_m(R\text{-}BINAP)]Y_n \qquad (I)$$

wherein R-BINAP represents a tertiary phosphine represented by formula (II):

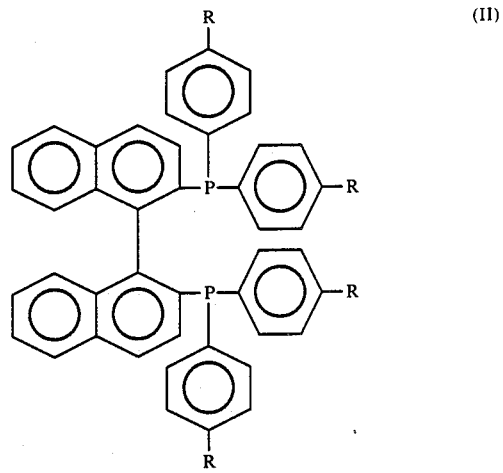

wherein R represents a hydrogen atom or a methyl group; X represents a halogen atom; L represents substituted or unsubstituted benzene or acetonitrile; Y represents a halogen atom, $ClO_4$, $PF_6$, $BPh_4$ (wherein Ph represents a phenyl group) or $BF_4$; when L is substituted or unsubstituted benzene, l represents 1, m represents 1, and n represents 1; and whe L is acetonitrile, when l is 1, then m represents 2, and n represents 1, and when l is 0, the m represents 4, and n represent 2. The complex exhibits excellent catalytic activity in asymmetric reactions to provide a product of high optical purity. The complex can be produced at low cost.

2 Claims, No Drawings

RUTHENIUM-PHOSHINE COMPLEX

FIELD OF THE INVENTION

This invention relates to a ruthenium-phosphine complex useful as a catalyst for various organic syntheses, particularly asymmetric hydrogenation.

BACKGROUND OF THE INVENTION

Various organic synthesis reactions using transition metal complexes as a catalyst have hitherto been developed and utilized for many purposes. In particular, there are a number of reports on asymmetric catalysts to be used in asymmetric syntheses, i.e., asymmetric isomerization, asymmetric hydrogenation, and the like. Of the reported asymmetric catalysts, metal complexes formed between metallic rhodium and an optically active tertiary phosphine are especially well known as catalysts for asymmetric hydrogenation. Such complexes typically include a rhodium-phosphine complex using 2,2'-bis(diphenylphosphino)-1,1'-binaphthyl (hereinafter abbreviated as BINAP) as a ligand as disclosed in JP-A-55-61937 (the term "JP-A" as used herein means an "unexamined published Japanese patent application"). Further, Inoue et al. report in *Chemistry Letters*, pp. 1007–1008 (1985) that citronellol can be obtained in an optical yield of 66% by asymmetric hydrogenation of geraniol or nerol using various rhodium-phosphine complexes.

On the other hand, known ruthenium complexes, though there are not so many reports as compared with rhodium complexes, include those having BINAP or 2,2'-bis(di-p-tolylphosphino)-1,1'-binaphthyl (hereinafter abbreviated as T-BINAP) as a ligand, e.g., $Ru_2Cl_4$(BINAP)$_2$NEt$_3$ (wherein Et represents an ethyl group, hereinafter the same) and $Ru_2Cl_4$(T-BINAP)$_2$NEt$_3$ as reported in Ikariya et al., *J. Chem. Soc. Chem. Commun.*, p. 922 (1985), Ru($O_2CR$)$_2$(BINAP) and Ru($O_2CR$)$_2$(T-BINAP) (wherein R represents a lower alkyl group, a lower alkyl-substituted phenyl group, etc.) as disclosed in JP-A-62-265293, and [RuH$_{80}$(R-BINAP)$_m$]X$_n$ (wherein R represents a hydrogen atom or a methyl group; X represents $ClO_4$, $BF_4$ or $PF_6$; when λ is 0, then m is 1, and n is 2; and when λ is 1, then m is 2, n is 1) as disclosed in JP-A-63-41487.

However, these conventional ruthenium complexes require complicated processes for the preparation thereof or the yields and stability of the preparation have not been satisfactory. Besides, the catalytic activity as well as duration of the activity of these complexes are still insufficient.

Although metallic rhodium provides excellent complex catalysts, it is expensive due to limitations in place and quantity of production When used as a catalyst component, it forms a large proportion in cost of the catalyst, ultimately resulting in an increase in cost of the final commercial products While metallic ruthenium is cheaper than metallic rhodium and appears promising as a catalyst component for advantageous industrial application, it still has problems in achievement of precise reactions and its range of application. Therefore, it has been keenly demanded to develop a catalyst which can be prepared easily at low cost, has high activity and durability, and catalyzes asymmetric reactions to attain high optical yields, i.e., to produce reaction products having high optical purity.

SUMMARY OF THE INVENTION

As a result of extensive investigations with the purpose of meeting the above-described industrial demand, the inventors have discovered a novel ruthenium complex having high catalytic activity which can be obtained in good yield through simple operations, and which is usable either for general syntheses when the ligand thereof is optically inactive or for asymmetric syntheses when the ligand thereof is optically active. The present invention has been completed based on this finding.

The present invention relates to a ruthenium-phosphine complex represented by formula (I)

$$[RuX_\lambda(L)_m(R\text{-BINAP})]Y_n \qquad (I)$$

wherein R-BINAP represents a tertiary phosphine represented by formula (II):

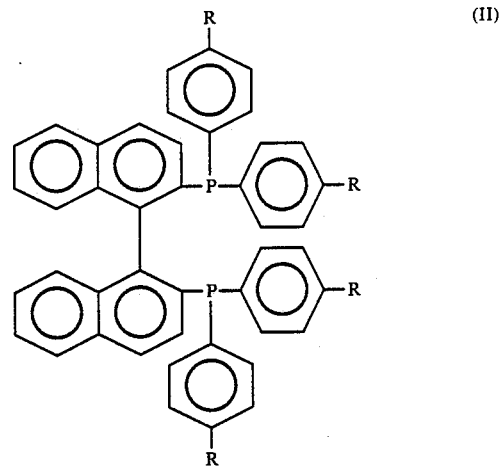

wherein R represents a hydrogen atom or a methyl group; X represents a halogen atom; L represents substituted or unsubstituted benzene or acetonitrile; Y represents a halogen atom, $ClO_4$, $PF_6$, $BPh_4$ (wherein Ph represents a phenyl group) or $BF_4$; when L is substituted or unsubstituted benzene, λ represents 1, m represents 1, and n represents 1; and when L is acetonitrile, when λ is 1, then m represents 2, and n represents 1, and when λ is 0, then m represents 4, and n represents 2.

DETAILED DESCRIPTION OF THE INVENTION

In formula (I), the substituted or unsubstituted benzene (hereinafter referred to as Ar) as represented by L is benzene which may be substituted with a lower alkyl group, a lower alkoxyl group, a carboalkoxyl group, a halogen atom, etc., e.g., benzene, toluene, xylene, trimethylbenzene, hexamethylbenzene, ethylbenzene, t-butylbenzene, p-cymene, cumene, methyl benzoate, methyl methylbenzoate, methyl chlorobenzoate, anisole, methylanisole, chlorobenzene, dichlorobenzene, trichlorobenzene, bromobenzene, and fluorobenzene.

The compound of formula (I) according to the present invention wherein L is a substituted or unsubstituted benzene nucleus can be prepared as follows. The compound wherein X and Y both represent a halogen atom, taking a chlorine atom, for instance, i.e., [RuCl(Ar)(BINAP)]Cl, can be quantitatively synthesized by reacting [RuCl$_2$(Ar)]$_2$ with BINAP in a solvent, e.g., methanol, ethanol, benzene, methylene chloride, etc., or a mixture thereof, at a temperature of from 25° C. to 50° C. for a period of from 30 minutes to 3 hours and removing the solvent from the reaction mixture by distillation under reduced pressure. The starting compound [RuCl$_2$(Ar)]$_2$ can be prepared by the processes disclosed in, e.g., G. Wikhaus, *J. Org. Chem.*, Vol 7, p. 487 (1976) or R.A. Zelonka, *Can. J. Chem.*, Vol. 50, p. 3643 (1972).

The compound wherein X and Y both represent a bromine atom or an iodine atom, i.e., [RuBr(Ar)(BINAP)]Br or [RuI(Ar)(BINAP)]I, can be quantitatively synthesized by (i) reacting [RuCl$_2$(Ar)]$_2$ with a salt represented by formula (III):

wherein M$^1$ represents Li, Na or K; and Z represents Br or I, in water as a solvent to obtain [RuZ$_2$(AR)]$_2$, or (ii) reacting [RuCl$_2$(Ar)]$_2$ with M$^1$Z in a mixed solvent of water and methylene chloride in the presence of a quaternary ammonium or phosphonium salt represented by formula (IV):

wherein R$^1$, R$^2$, R$^3$, and R$^4$ each represents an alkyl group having from 1 to 16 carbon atoms, a phenyl group or a benzyl group; Q represents a nitrogen atom or a phosphorus atom; and X' represents a halogen atom, as a phase transfer catalyst by stirring at room temperature to obtain [RuZ$_2$(Ar)]$_2$, and then reacting the resulting [RuZ$_2$(Ar)]$_2$ with BINAP in a solvent, e.g., methanol, ethanol, benzene, methylene chloride, etc., or a mixture thereof at a temperature of from 25° C. to 50° C. for a period of from 30 minutes to 3 hours, followed by removing the solvent by distillation under reduced pressure.

The phase transfer catalyst of formula (IV) which can be used includes those described in W.P. Weber and G.W. Gokel (translated by Iwao Tabushi and Takako Nishitani), *Sokan Ido Shokubai*, 1st Ed., Kagaku Dojin K.K., (Sept. 5, 1978).

The compound wherein X is a halogen atom (a chlorine atom being taken as an instance), and Y represents ClO$_4$, PF$_6$, BPh$_4$ or BF$_4$ can be quantitatively obtained by, for example, adding a salt represented by formula:

MY wherein M represents Na, K, Li, Mg or Ag; and Y represents ClO$_4$, PF$_6$, BPh$_4$ or BF$_4$, to a solution of [(RuCl(Ar)(BINAP)]Cl in a solvent, e.g., methanol, ethanol, acetone, methylene chloride, etc., followed by stirring, separating the small amount of insoluble matters, and concentrating the filtrate to dryness.

The compound wherein L represents acetonitrile, and X and Y both represent a halogen atom (a chlorine atom being taken as an instance), i.e., [RuCl(acetonitrile)$_2$(BINAP)]Cl, can be obtained, for example, as follows. An [RuCl(Ar)(BINAP)]Cl complex is dissolved in acetonitrile, the solution is heated at from 25° C. to 50° C. for 10 to 24 hours, and excess acetonitrile is removed by distillation, followed by drying to a solid to obtain a crude complex, which is then recrystallized from methylene chloride to obtain the desired compound in a yield of 90% or more.

Alternatively, [Ru(acetonitrile)$_4$(BINAP)]Y$_2$ can be obtained in a yield of 90% or more by dissolving a [RuCl(Ar)(BINAP)]Cl complex, for example, in a mixed solvent of acetonitrile and methanol, ethanol, acetone or methylene chloride, adding MY to the solution, heating the solution at 25° C. to 50° C. for 10 to 24 hours, removing the solvent by distillation, and recrystallizing the residue from methylene chloride.

In the preparation of the complexes of the present invention according to any of the above-described processes, the solvent used in the synthesis reaction or recrystallization of the crude product is sometimes incorporated into the finally obtained crystals. For example, the complex obtained in Example 1 hereinafter described contained double the molar quantity of ethanol used as a solvent for synthesis; and the complex obtained in Example 4 hereinafter described contained half the molar quantity of methylene chloride used for recrystallization. In other cases, for example, in Example 2 hereinafter described, the solvent used was not incorporated into the product at all. Notwithstanding, the incorporation of the solvent into the product does not give rise to any problem in the synthesis of the complex and for use as a catalyst of asymmetric hydrogenation.

The ruthenium-phosphine complex thus obtained was confirmed to be a pure complex by analyses, such as spectral analysis. The complex according to the present invention is a stable compound and, when used in asymmetric hydrogenation, exhibits very high catalytic activity. In more detail, asymmetric hydrogenation rapidly proceeds by using the complex at a molar concentration of from 1/100 to 1/10000 based on a substrate to produce a desired hydrogenation product having high purity and optical purity. For example, asymmetric hydrogenation of methyl acetoacetate as a substrate in the presence of the catalyst gives methyl 3-hydroxybutyrate having a purity of 100% and an optical purity of from 97 to 99%. Thus, the ruthenium-phosphine complex according to the present invention produces very excellent results as an industrial catalyst.

The present invention will now be illustrated in greater detail with reference to Examples and Use Examples, but it should be understood that at the present invention is not deemed to be limited thereto. All the percents in these examples are by weight unless otherwise indicated.

EXAMPLE 1

Synthesis of [RuCl(benzene)(S)-BINAP)]Cl (Chloro-π-benzene-[2,2'-bis(diphenylphosphino)-1,1'-binaphthyl]ruthenium Chloride)

In 10 ml of 90% ethanol were dissolved 2.6 g (10 mmole) of RuCl$_3$·3H$_2$O and 10 ml (105 mmole) of 1,3cyclohexadiene, followed by heating at 35° C. for 5 hours. The precipitated crystals were collected by filtration, washed with methanol, and dried to obtain 1.87 g (yield: 75%) of [Ru(benzene)Cl$_2$]$_2$(μ-dichloro-π-benzene-ruthenium) as a reddish brown solid.

In s Schlenk's tube were charged 0.33 g (0.66 mmole) of [Ru(benzene)Cl$_2$]$_2$ and 0.82 g (1.31 mmole) of (S)-BINAP. After displacing the atmosphere with argon, 150 ml of ethanol and 20 ml of benzene were added thereto, followed by heating at 50° C. for 45 minutes. The reaction solution was filtered through Celite, and the filtrate was concentrated to dryness to obtain 1.14 g (yield: 90%) of [RuCl(benzene)(S)-BINAP)]Cl as a yellow solid.

Melting Point: 114 to 125° C. (with decomposition) Elemental Analysis for $C_{50}H_{38}Cl_2P_2Ru$: Calcd. (%): C 67.21, H 5.22; Found (%): C 66.48, H 4.90.

The $^{31}P$ nuclear magnetic resonance spectrum ($^{31}P$-NMR) was determined using "JNM-GX400" manufactured by JEOL Ltd. Chemical shifts were determined using 85% $H_3PO_4$ as an external standard. $^{31}P$ NMR(CDCl$_3$)δppm: 30.3 (d, J=64.6 Hz), 38.3 (d, J=64.6 Hz).

EXAMPLE 2

Synthesis of [RuCl(benzene)((S)-T-BINAP)]BF$_4$
(Chloro-π-benzene-[2,2'-bis(di-p-tolylphosphino)-1,1'-binaphthyl]ruthenium Tetrafluoroborate)

In 20 ml of methylene chloride was dissolved 0.03 g (0.15 mmole) of AgBF$_4$, and 0.13 g (0.14 mmole) of [RuCl(benzene)((S)-T-BINAP)]Cl prepared in the same manner as in Example 1 and 20 ml of methylene chloride were added thereto, followed by stirring for 1 hour. The reaction solution was filtered through Celite, and the filtrate was concentrated to dryness to obtain 0.13 g (yield: 95%) of [RuCl(benzene)((S)-T-BINAP)]BF$_4$ as a yellowish brown solid.

Elemental Analysis for $C_{54}H_{46}BClF_4P_2Ru$: Calcd. (%): C 66.17; H 4.73; Found (%): C 65.73; H 4.48.

$^{31}P$-NMR(CDCl$_3$)δppm: 28.4 (d, J=64.5 Hz), 36.2 (d, J=64.5 Hz).

EXAMPLE

Synthesis of [RuCl(p-cymene)((S)-BINAP)]Cl
(Chloro-π-p-cymene-[2,2'-bis(diphenylphosphino)-1,1'-binaphthyl]ruthenium Chloride)

One gram of RuCl$_3$·3H$_2$O, 30 ml of 90% ethanol, and 5 ml (31 mmole) of p-mentha-1,5-diene were stirred at 45 to 50° C. for 5 hours. The precipitated crystals were collected by filtration, washed with methanol, and dried to obtain 0.79 g (yield: 54%) of [Ru(p-cymene)Cl$_2$]$_2$ as an orange solid.

The resulting [Ru(p-cymene)Cl$_2$]$_2$ (0.26 g, 0.43 mmole), 0.53 g (0.85 mmole) of (S)-BINAP, and 60 ml of ethanol were stirred at 50° C. for 1 hour. The reaction solution was filtered through Celite, and the filtrate was concentrated to dryness to obtain 0.77 g (yield: 97%) of [RuCl(p-cymene)((S)-BINAP)]Cl as a yellowish brown solid.

Elemental Analysis for $C_{48}H_{38}N_2Cl_2P_2Ru$: Calcd. (%): C 69.83; H 4.99; Found (%): C 70.47; H 5.29.

$^{31}P$-NMR(CDCl$_3$)δppm: 24.5 (d, J=62.6 Hz), 41.2 (d, J=62.6 Hz).

EXAMPLE 4

Synthesis of [RuCl(acetonitrile)$_2$((S)-BINAP)]Cl
(Chloro-bisacetonitrile-[2,2'-bis(diphenyl-phosphino)-1,1'-binaphthyl]ruthenium Chloride)

In a 80 ml-volume Schlenk's tube was charged 0.1 g (0.11 mmole) of [RuCl(benzene)(S)-BINAP)]Cl obtained in Example 1, and 20 ml of acetonitrile was added thereto, followed by heating at 50° C. for 24 hours while stirring to obtain a yellow clear solution. The solvent was removed under reduced pressure to obtain a yellow solid, which was then recrystallized from methylene chloride-diethyl ether to obtain 0.09 g (yield: 80%) of [RuCl(acetonitrile)$_2$((S)-BINAP)]Cl as a yellow solid. Elemental Analysis for $C_{48}H_{38}N_2Cl_2P_2Ru$: Calcd. (%): C 65.76; H 4.33; N 3.19; Found (%): C 65.53; H 4.69; N 3.32.

$^{31}P$-NMR(CDCl$_3$)δppm: 51.3 (d, J=35.2 Hz), 54.4 (d, J=35.2 Hz).

EXAMPLE 5

Synthesis of [RuCl(acetonitrile)$_4$((S)-BINAP)](BF$_4$)$_2$
(Tetraacetonitrile-[2,2'-bis(diphenylphosphino)-1,1'-binaphthyl]ruthenium-ditetrafluoroborate)

In 20 ml of methylene chloride were dissolved 0.15 g (0.17 mmole) of [RuCl(benzene)(S)-BINAP)]Cl as obtained in Example 1 and 20 ml of acetonitrile, and 0.07 g (0.36 mmole) of AgBF$_4$ was added thereto, followed by heating at 50° C. for 12 hours. The solvent was removed by distillation, and the residue was extracted with methylene chloride. The solvent was removed from the extract by distillation to obtain 0.15 g (yield: 88%) of [RuCl(acetonitrile)$_4$((S)-BINAP)](BF$_4$)$_2$.

Elemental Analysis for $C_{52}H_4N_4B_2F_8P_2Ru$: Calcd. (%): C 58.83; H 4.18; N 5.28; Found (%): C 58.96; H 4.25; N 5.53.

$^{31}P$-NMR(CDCl$_3$)δppm: 45.7

EXAMPLE 6

Synthesis of [RuI(p-cymene)((R)-BINAP)]I
(Iodo-π-p-cymene-[2,2'-bis(diphenylphosphino)-1,1'-binaphthyl]ruthenium Iodide)

In 87 ml of methylene chloride were dissolved 3.5 g (0.11 mmole) of [Ru(p-cymene)Cl$_2$]$_2$ as synthesized in Example 3 and 120 mg of tetramethylammonium iodide, and a solution of 18.3 g (110 mmole) of potassium iodide in 87 ml of water was added dropwise thereto, followed by stirring at room temperature for 16 hours. The organic layer separated was washed three times with 120 ml portions of water, and the solvent was removed by distillation, followed by drying to obtain 4.9 g (yield: 89%) of [Ru(p-cymene)I$_2$]$_2$ (μ-diiodo-π-p-cymene-rhutenium) as a deep purple solid.

In a mixture of 45 ml of ethanol and 23 ml of methylene chloride were dissolved 0.25 g (0.26 mmole) of the resulting [Ru(p-cymene)I$_2$]$_2$ and 0.35 g (0.56 mmole) of (R)-BINAP, and the solution was stirred at 50° C. for 1 hour. The reaction solution was filtered through Celite, and the filtrate was concentrated to dryness to obtain 0.58 g (yield: 100%) of [RuI(p-cymene)((R)- C BINAP)]as a brown solid.

Elemental Analysis for $C_{54}H_{46}I_2P_2Ru$: Calcd. (%): C 58.34; H 4.17; Found (%): C 57.96; H 3.73.

$^{31}P$-NMR (CDCl$_3$)δppm: 24.8 (J=60.2 Hz), 41.6 (J=60.0 Hz).

EXAMPLES 7 TO 25

Ruthenium-phosphine complexes of Table 1 below were synthesized in the same manner as in Examples 1 to 6, except for varying the starting materials. Analytical values of the resulting complexes are shown in Table 1. The elemental analytical values shown in Table 1 are for the products from which any solvent, if present due to incorporation during the preparation, has been removed.

TABLE 1

| Example No. | Ruthenium-Phosphine Complex (Molecular Formula) | Element | Elemental Analysis (%) Calcd. | Found | $^{31}$P-NMR (δ ppm) |
|---|---|---|---|---|---|
| 7 | [RuCl(benzene)((S)-BINAP)]BF$_4$ $C_{50}H_{38}ClBF_4P_2Ru$ | C H | 60.71 4.00 | 60.67 4.02 | 29.8 (d, J = 64.6) 37.8 (d, J = 64.6) |
| 8 | [RuCl(benzene)((S)-BINAP)]BPh$_4$ $C_{74}H_{58}ClBP_2Ru$ | C H | 76.36 5.13 | 76.71 5.03 | 30.2 (d, J = 62.6) 37.9 (d, J = 62.6) |
| 9 | [RuCl(benzene)((S)-T-BINAP)]Cl $C_{54}H_{46}Cl_2P_2Ru$ | C H | 69.69 5.30 | 69.85 5.18 | 28.9 (d, J = 62.6) 36.7 (d, J = 62.6) |
| 10 | [RuCl(p-cymene)((S)-BINAP)]BF$_4$ $C_{54}H_{46}ClBF_4P_2Ru$ | C H | 66.17 4.73 | 66.31 4.66 | 24.2 (d, J = 62.6) 40.4 (d, J = 62.6) |
| 11 | [RuCl(p-cymene)((S)-T-BINAP)]Cl $C_{58}H_{54}Cl_2P_2Ru$ | C H | 70.72 5.52 | 70.94 5.43 | 23.0 (d, J = 62.6) 39.3 (d, J = 62.6) |
| 12 | [RuCl(p-cymene)((S)-T-BINAP)]BF$_4$ $C_{58}H_{54}ClBF_4P_2Ru$ | C H | 67.22 5.25 | 67.31 5.08 | 23.1 (d, J = 62.6) 39.0 (d, J = 62.6) |
| 13 | [RuCl(benzene)((R)-BINAP)]ClO$_4$ $C_{50}H_{38}O_4Cl_2P_2Ru$ | C H | 64.11 4.09 | 64.28 3.87 | 30.4 (d, J = 63.5) 38.2 (d, J = 63.5) |
| 14 | [RuCl(benzene)((R)-BINAP)]PF$_6$ $C_{50}H_{38}ClF_6P_3Ru$ | C H | 61.14 3.90 | 61.44 3.77 | 30.2 (d, J = 63.5) 38.0 (d, J = 63.5) |
| 15 | [RuCl(benzene)((R)-T-BINAP)]ClO$_4$ $C_{54}H_{46}O_4Cl_2P_2Ru$ | C H | 65.32 4.67 | 65.57 4.51 | 28.5 (d, J = 63.3) 36.3 (d, J = 63.3) |
| 16 | [RuCl(benzene)((R)-T-BINAP)]PF$_6$ $C_{54}H_{46}ClF_6P_3Ru$ | C H | 62.46 4.47 | 62.62 4.33 | 28.4 (d, J = 63.2) 38.0 (d, J = 62.9) |
| 17 | [RuCl(p-cymene)((R)-BINAP)]ClO$_4$ $C_{54}H_{46}Cl_2O_4P_2Ru$ | C H | 65.32 4.67 | 65.46 4.61 | 25.6 (d, J = 61.6) 41.5 (d, J = 61.6) |
| 18 | [RuCl(p-cymene)((R)-BINAP)]PF$_6$ $C_{54}H_{46}ClF_6P_3Ru$ | C H | 62.46 4.46 | 62.39 4.56 | 25.4 (d, J = 61.6) 41.3 (d, J = 61.6) |
| 19 | [RuCl(p-cymene)((R)-BINAP)]ClO$_4$ $C_{58}H_{54}ClO_4P_2Ru$ | C H | 66.41 5.19 | 66.37 5.32 | 23.7 (d, J = 61.4) 39.4 (d, J = 61.4) |
| 20 | [RuCl(p-cymene)((R)-T-BINAP)]PF$_6$ $C_{58}H_{54}ClF_6P_3Ru$ | C H | 63.65 4.97 | 63.57 5.10 | 23.6 (d, J = 61.5) 39.2 (d, J = 61.5) |
| 21 | [RuCl(p-cymene)((R)-T-BINAP)]BPh$_6$ $C_{82}H_{74}ClBP_2Ru$ | C H | 77.63 5.88 | 77.48 5.94 | 23.5 (d, J = 60.6) 39.1 (d, J = 60.6) |
| 22 | [RuCl(benzene)((R)-T-BINAP)]BPh$_4$ $C_{78}H_{66}ClBP_2Ru$ | C H | 77.26 5.49 | 77.41 5.25 | 28.3 (d, J = 64.4) 35.8 (d, J = 64.4) |
| 23 | [RuBr(benzene)((S)-BINAP)]Br $C_{50}H_{38}Br_2P_2Ru$ | C H | 62.45 3.98 | 62.71 3.86 | 29.8 (d, J = 62.6) 37.1 (d, J = 62.6) |
| 24 | [RuI(benzene)((S)-BINAP)]I $C_{50}H_{38}I_2P_2Ru$ | C H | 56.89 3.63 | 57.01 3.39 | 28.2 (d, J = 61.0) 36.1 (d, J = 61.0) |
| 25 | [RuCl(methyl benzoate)((S)-BINAP)]Cl $C_{52}H_{40}Cl_2O_2P_2Ru$ | C H | 67.10 4.33 | 67.22 4.07 | 26.5 (d, J = 63.0) 37.9 (d, J = 63.0) |

USE EXAMPLE 1

In a 50 ml-volume autoclave were charged 0.96 g (8.3 mmole) of methyl acetoacetate and 8 ml of methanol, and 2.4 ml (2.8x10-3 mmole) of [RuCl(benzene)((S)-BINAP)]Cl as obtained in Example 1 was added thereto under an argon stream, and a hydrogenation reaction was conducted at 20° C. and at a hydrogen pressure of 100 kg/cm$^2$ for 50 hours. After the solvent was removed by distillation, the residue was subjected to distillation to obtain 0.7 g (yield: 73%) of methyl 3-hydroxybutyrate as a fraction having a boiling point of 63° C./10 mmHg.

The resulting product was reacted with (R)-(+)-α-methoxy-α-trifluoromethyl-phenylacetyl chloride to synthesize an ester. The ester was separated into diastereomers and analyzed by high performance liquid chromatography using a column "Nuclosil ® 100-3" produced by Chemco Co. (4.6 mm in diameter×300 mm in height), a 8:2 (by volume) mixture of hexane-diethyl ether as an eluent (flow rate: 1 ml/min), and a UV detector (detection wavelength: 254 nm). As a result, the starting alcohol was found to be a mixture of 98.8% of methyl (S)-(+)-3-hydroxybutyrate and 1.2% of methyl (R)-(−)-3-hydroxybutyrate, and the optical yield was thus found to be 97.6% ee.

USE EXAMPLES 2 TO 25

Methyl 3-hydroxybutyrate was prepared by conducting asymmetric hydrogenation of methyl acetoacetate in the same manner as in Use Example 1, except for using each of the ruthenium-phosphine complexes obtained in Examples 2 to 25 as a catalyst. The results obtained are shown in Table 2 below.

TABLE 2

| Use Example No. | Ruthenium-Phosphine Complex | Reaction Conditions Substrate/Catalyst (mol/mol) | Hydrogen Pressure (kg/cm$^2$) | Temperature (°C.) | Time (hr) | Reaction Results Conversion (%) | Yield (%) | Optical Yield (% ee) | Absolute Configuration |
|---|---|---|---|---|---|---|---|---|---|
| 2 | [RuCl(benzene)((S)-T-BINAP)]BF$_4$ | 3000 | 95 | 58 | 48 | 100 | 98 | 84.4 | S |
| 3 | [RuCl(p-cymene)((S)-BINAP)]Cl | 500 | 101 | 60 | 48 | 86 | 82 | 87.2 | S |
| 4 | [RuCl(acetonitrile)$_2$((S)-BINAP)]Cl | 1000 | 97 | 55 | 156 | 91 | 69 | 93.2 | S |
| 5 | [Ru(acetonitrile)$_4$((S)-BINAP)](BF$_4$)$_2$ | 100 | 100 | 60 | 72 | 78 | 65 | 81.6 | S |
| 6 | [RuI(p-cymene)((R)-BINAP)]I | 5000 | 100 | 50 | 24 | 100 | 99 | 99.3 | R |
| 7 | [RuCl(benzene)((S)-BINAP)]BF$_4$ | 2000 | 100 | 60 | 40 | 100 | 97 | 84.2 | S |
| 8 | [RuCl(benzene)((S)-BINAP)]BPh$_4$ | 100 | 100 | 60 | 48 | 54 | 50 | 68.6 | S |
| 9 | [RuCl(benzene)((S)-T-BINAP)]Cl | 3000 | 100 | 60 | 48 | 100 | 98 | 88.6 | S |
| 10 | [RuCl(p-cymene)((S)-BINAP)]BF$_4$ | 1000 | 100 | 60 | 48 | 78 | 75 | 82.8 | S |
| 11 | [RuCl(p-cymene)((S)-T-BINAP)]Cl | 500 | 89 | 40 | 48 | 65 | 61 | 83.8 | S |
| 12 | [RuCl(p-cymene)((S)-T-BINAP)]BF$_4$ | 1000 | 100 | 60 | 48 | 84 | 83 | 84.6 | S |
| 13 | [RuCl(benzene)((R)-BINAP)]ClO$_4$ | 1000 | 100 | 60 | 48 | 100 | 98 | 89.2 | R |

TABLE 2-continued

| Use Example No. | Ruthenium-Phosphine Complex | Reaction Conditions | | | | Reaction Results | | | |
|---|---|---|---|---|---|---|---|---|---|
| | | Substrate/ Catalyst (mol/mol) | Hydrogen Pressure (kg/cm$^2$) | Temperature (°C.) | Time (hr) | Conversion (%) | Yield (%) | Optical Yield (% ee) | Absolute Configuration |
| 14 | [RuCl(benzene)((R)-BINAP)]PF$_6$ | 1000 | 100 | 60 | 48 | 100 | 98 | 87.6 | R |
| 15 | [RuCl(benzene)((R)-T-BINAP)]ClO$_4$ | 1000 | 100 | 60 | 48 | 100 | 98 | 90.2 | R |
| 16 | [RuCl(benzene)((R)-T-BINAP)]PF$_6$ | 1000 | 100 | 60 | 48 | 100 | 98 | 88.2 | R |
| 17 | [RuCl(p-cymene)((R)-BINAP)]ClO$_4$ | 1000 | 100 | 60 | 48 | 89 | 86 | 88.8 | R |
| 18 | [RuCl(p-cymene)((R)-BINAP)]PF$_6$ | 1000 | 100 | 60 | 48 | 84 | 82 | 86.8 | R |
| 19 | [RuCl(p-cymene)((R)-T-BINAP)]ClO$_4$ | 1000 | 100 | 60 | 48 | 100 | 98 | 87.8 | R |
| 20 | [RuCl(p-cymene)((R)-T-BINAP)]PF$_6$ | 1000 | 100 | 60 | 48 | 87 | 83 | 83.4 | R |
| 21 | [RuCl(p-cymene)((S)-T-BINAP)]BPh$_4$ | 100 | 100 | 60 | 48 | 61 | 58 | 71.4 | S |
| 22 | [RuCl(benzene)((R)-T-BINAP)]BPh$_4$ | 100 | 97 | 60 | 48 | 60 | 57 | 73.8 | R |
| 23 | [RuCl(benzene)((S)-BINAP)]Br | 2000 | 100 | 50 | 48 | 100 | 98 | 97.0 | S |
| 24 | [RuI(benzene)((S)-BINAP)]I | 2000 | 100 | 50 | 48 | 100 | 97 | 99.0 | S |
| 25 | [RuCl(methyl benzoate)((S)-BINAP)]Cl | 500 | 100 | 60 | 72 | 82 | 80 | 84.8 | S |

The present invention provides a novel ruthenium-phosphine complex exhibiting excellent performance properties as a catalyst for various organic syntheses, and particularly asymmetric hydrogenation. For example, it shows industrially superior results in selective hydrogenation of olefins as well as in catalytic activity. Further, the complex according to the present invention can be produced at lower cost as compared with the conventional rhodium catalysts, making a contribution to reduction of product price and, thus, has a high industrial value.

While the invention has been described in detail and with reference to specific embodiments thereof, it will be apparent to one skilled in the art that various changes and modifications can be made therein without departing from the spirit and scope thereof.

What is claimed is:

1. A ruthenium-phosphine complex represented by formula (I)

[RuX$_\lambda$(L)$_m$(R-BINAP)]Y$_n$    (I)

wherein R-BINAP represents a tertiary phosphine represented by formula (II):

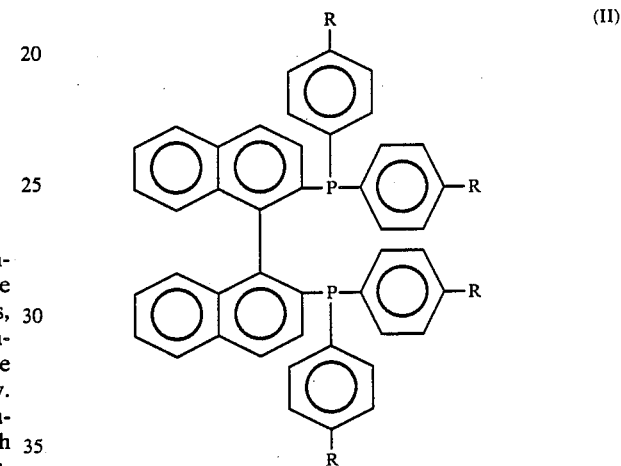

wherein R represents a hydrogen atom or a methyl group; X represents a halogen atom; L represents substituted or unsubstituted benzene or acetonitrile; Y represents a halogen atom, ClO$_4$, PF$_6$, BPh$_4$, wherein Ph represents a phenyl group, or BF$_4$; when L is substituted or unsubstituted benzene, λ represents 1, m represents 1, and n represents 1; and when L is acetonitrile, when λ is 1, then m represents 2, and n represents 1, and when λ is 0, then m represents 4, and n represents 2.

2. A ruthenium-phosphine complex as in claim 1, wherein L represents benzene or a benzene substituted with a lower alkyl group, a lower alkoxy group, a carboalkoxy group, or a halogen atom.

* * * * *